US008206950B2

(12) United States Patent
Liao et al.

(10) Patent No.: US 8,206,950 B2
(45) Date of Patent: *Jun. 26, 2012

(54) FUSION ANTIGEN USED AS VACCINE AND METHOD OF MAKING THEM

(75) Inventors: Chao-Wei Liao, Shin-Chu (TW); Chung-Nan Weng, Miaoli County (TW); Hsiu-Kang Chang, Taipei (TW)

(73) Assignee: Animal Technology Institute Taiwan, Miaoli (TW)

( * ) Notice: Subject to any disclaimer, the term of this patent is extended or adjusted under 35 U.S.C. 154(b) by 534 days.

This patent is subject to a terminal disclaimer.

(21) Appl. No.: 12/276,334

(22) Filed: Nov. 22, 2008

(65) Prior Publication Data

US 2009/0088556 A1    Apr. 2, 2009

Related U.S. Application Data

(63) Continuation-in-part of application No. 11/948,327, filed on Nov. 30, 2007, now Pat. No. 7,595,054, which is a continuation-in-part of application No. 10/457,574, filed on Jun. 9, 2003, now Pat. No. 7,335,361.

(51) Int. Cl.
*C12P 21/00* (2006.01)
*A61K 39/104* (2006.01)
*A61K 39/12* (2006.01)

(52) U.S. Cl. ............ 435/69.7; 435/69.1; 435/69.3; 435/71.2; 424/184.1; 424/204.1; 424/260.1

(58) Field of Classification Search ............... None
See application file for complete search history.

(56) References Cited

U.S. PATENT DOCUMENTS

| 5,854,044 | A | * | 12/1998 | Pastan et al. | ............... 435/194 |
| 5,916,879 | A | | 6/1999 | Webster | |
| 5,972,659 | A | * | 10/1999 | Haynes et al. | ............... 435/69.7 |
| 6,001,612 | A | | 12/1999 | Yang | |
| 2004/0247617 | A1 | | 12/2004 | Liao | |
| 2005/0009008 | A1 | | 1/2005 | Robinson | |
| 2007/0036824 | A1 | | 2/2007 | Bryan | |
| 2007/0243587 | A1 | | 10/2007 | Liao | |
| 2008/0206271 | A1 | * | 8/2008 | Liao et al. | ............... 424/192.1 |

FOREIGN PATENT DOCUMENTS

| WO | WO 00/53787 A1 * | 3/2000 |
| WO | 2003/018055 | 3/2003 |
| WO | 2004/041851 | 5/2004 |
| WO | 2005/047315 | 5/2005 |
| WO | 2005/107797 | 11/2005 |

OTHER PUBLICATIONS

Rino Rappuoli and Antonello Covacci , "Reverse Vaccinology and Genomics," Science Oct. 24, 2003, vol. 302. No. 5645, p. 602.
Bardiya and Bae, (2005) "Influenza vaccines: recent advances in production technologies," Applied Microbiology and Biotechnology 67(3):299-305.
Liao et al., "Fusion Protein Vaccine by Domains of Bacterial Exotoxin Linked with a Tumor Antigen Generates Potent Immunologic Responses and Antitumor Effects" Cancer Res 65:(19), 9089-9098 (2005).
Amela I, Cedano J, Querol E (2007) Pathogen Proteins Eliciting Antibodies Do Not Share Epitopes with Host Proteins: A Bioinformatics Approach. PLoS ONE 2(6): e512. doi:10.1371/journal.pone.0000512.

* cited by examiner

*Primary Examiner* — Stacy B. Chen
(74) *Attorney, Agent, or Firm* — Hsiu-Ming Saunders Intellectual Property Connections, Inc.

(57) ABSTRACT

Fusion antigen used as vaccine and method of making them. The method includes: (1) selecting a segment of a virus protein sequence that contains a least one epitope; (2) engineering a DNA fragment encoding the selected segment of the virus protein; (3) inserting the DNA fragment into a *Pseudomonas* Exotoxin A (PE) vector to obtain a chimeric gene plasmid, and expressing the chimeric gene plasmid in a host cell to obtain the chimeric vaccinal virus antigen. The PE vector contains a PE fragment, which has a binding domain and a translocating domain, and a carboxyl terminal moiety, which includes an endoplasmic reticulum retention sequence. The DNA fragment encoding the selected segment of the virus protein is inserted between the PE fragment and the carboxyl terminal moiety.

11 Claims, 5 Drawing Sheets

FIG. 4

SEQUENCE LISTING

```
<160> NUMBER OF SEQ ID NOS: 112

<210> SEQ ID NO 1
<211> LENGTH: 120
<212> TYPE: PRT
<213> ORGANISM: Avian influenza virus

<400> SEQUENCE: 1

Met Asp Ser Asn Thr Val Ser Ser Phe Gln Val Asp Cys Phe Leu Trp
1               5                   10                  15

Arg Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Glu Ser Asp Glu Ala Leu Lys Met Thr
65                  70                  75                  80

Ile Ala Ser Val Pro Ala Pro Arg Tyr Leu Thr Glu Met Thr Leu Glu
                85                  90                  95

Glu Met Ser Arg Asp Trp Leu Met Leu Ile Pro Lys Gln Lys Val Thr
            100                 105                 110

Gly Ser Leu Cys Ile Arg Met Asp
        115                 120

<210> SEQ ID NO 2
<211> LENGTH: 70
<212> TYPE: PRT
<213> ORGANISM: Avian influenza virus

<400> SEQUENCE: 2

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Ile Ser Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Lys Lys Asp Glu
    50                  55                  60

Leu Arg Asp Glu Leu Lys
65                  70
```

<210> SEQ ID NO 3
<211> LENGTH: 107
<212> TYPE: PRT
<213> ORGANISM: Avian influenza virus

<400> SEQUENCE: 3

Arg Met Val Leu Ser Ala Phe Asp Glu Arg Arg Asn Arg Tyr Leu Glu
1               5                   10                  15

Glu His Pro Ser Ala Gly Lys Asp Pro Lys Lys Thr Gly Gly Pro Ile
            20                  25                  30

Tyr Arg Arg Arg Asp Gly Lys Trp Val Arg Glu Leu Ile Leu Tyr Asp
        35                  40                  45

Lys Glu Glu Ile Arg Arg Ile Trp Arg Gln Ala Asn Asn Gly Glu Asp
50                  55                  60

Ala Thr Ala Gly Leu Thr His Leu Met Ile Trp His Ser Asn Leu Asn
65                  70                  75                  80

Asp Ala Thr Tyr Gln Arg Thr Arg Ala Leu Val Arg Thr Gly Met Asp
                85                  90                  95

Pro Arg Met Cys Ser Lys Lys Asp Glu Leu Lys
            100                 105

<210> SEQ ID NO 4
<211> LENGTH: 140
<212> TYPE: PRT
<213> ORGANISM: Avian influenza virus

<400> SEQUENCE: 4

Thr Leu Pro Arg Arg Ser Gly Ala Ala Gly Ala Ala Val Lys Gly Val
1               5                   10                  15

Gly Thr Met Val Met Glu Leu Ile Arg Met Ile Lys Arg Gly Ile Asp
            20                  25                  30

Asp Arg Asn Phe Trp Arg Gly Glu Asn Gly Arg Arg Thr Arg Ile Ala
        35                  40                  45

Tyr Glu Arg Met Cys Asn Ile Leu Lys Gly Lys Phe Gln Thr Ala Ala
50                  55                  60

Gln Arg Ala Met Met Asp Lys Lys Asp Glu Leu Leu Ile Phe Leu Ala
65                  70                  75                  80

Arg Ser Ala Leu Ile Leu Arg Gly Ser Val Ala His Lys Ser Cys Leu
                85                  90                  95

Pro Ala Cys Val Tyr Gly Leu Ala Val Ala Ser Gly Tyr Asp Phe Glu
            100                 105                 110

Arg Glu Gly Tyr Ser Leu Val Gly Ile Asp Pro Phe Arg Leu Leu Gln
        115                 120                 125

Asn Ser Gln Val Phe Ser Leu Arg Asp Glu Leu Lys
    130                 135                 140

<210> SEQ ID NO 5
<211> LENGTH: 148
<212> TYPE: PRT
<213> ORGANISM: Avian influenza virus

<400> SEQUENCE: 5

Phe Ile Arg Gly Thr Arg Val Val Pro Arg Gly Gln Leu Ser Thr Arg
1               5                   10                  15

Gly Val Gln Ile Ala Ser Asn Glu Asn Met Glu Ala Met Asp Ser Asn
            20                  25                  30

Thr Leu Glu Leu Arg Ser Arg Tyr Trp Ala Ile Arg Thr Arg Ser Gly

```
                     35                  40                  45
Gly Asn Leu Glu Asp Lys Lys Thr Phe Ser Val Gln Arg Asn Leu Pro
 50                  55                  60

Phe Glu Arg Ala Thr Ile Met Ala Val Phe Thr Gly Asn Thr Glu Gly
 65                  70                  75                  80

Arg Thr Ser Asp Met Arg Thr Glu Ile Ile Arg Met Met Glu Ser Ala
                 85                  90                  95

Arg Pro Glu Asp Val Ser Phe Gln Gly Arg Gly Val Phe Glu Leu Ser
                100                 105                 110

Asp Glu Lys Ala Thr Asn Pro Ile Val Pro Ser Phe Asp Met Asn Asn
            115                 120                 125

Glu Gly Ser Tyr Phe Phe Gly Asp Asn Ala Glu Glu Tyr Tyr Asn Arg
        130                 135                 140

Asp Glu Leu Lys
145

<210> SEQ ID NO 6
<211> LENGTH: 150
<212> TYPE: PRT
<213> ORGANISM: Avian influenza virus

<400> SEQUENCE: 6

Ala Asn Asp Leu Cys Tyr Pro Gly Asp Phe Asn Asp Tyr Glu Glu Leu
  1               5                  10                  15

Lys His Leu Leu Ser Arg Ile Asn His Phe Glu Lys Ile Gln Ile Ile
                 20                  25                  30

Pro Lys Ser Ser Trp Ser Asn His Glu Ala Ser Ser Gly Val Ser Ser
             35                  40                  45

Ala Cys Pro Tyr Leu Gly Lys Ser Ser Phe Phe Arg Asn Val Val Trp
 50                  55                  60

Leu Ile Lys Lys Asn Asn Ala Tyr Pro Thr Ile Lys Arg Ser Tyr Asn
 65                  70                  75                  80

Asn Thr Asn Gln Glu Asp Leu Leu Val Leu Trp Gly Ile His His Pro
                 85                  90                  95

Asn Asp Ala Ala Glu Gln Thr Lys Leu Tyr Gln Asn Pro Thr Thr Tyr
            100                 105                 110

Ile Ser Val Gly Thr Ser Thr Leu Asn Gln Arg Leu Val Pro Lys Ile
        115                 120                 125

Ala Thr Arg Ser Lys Val Asn Gly Gln Ser Gly Arg Met Glu Phe Phe
    130                 135                 140

Trp Thr Ile Leu Lys Pro
145                 150

<210> SEQ ID NO 7
<211> LENGTH: 70
<212> TYPE: PRT
<213> ORGANISM: Avian influenza virus

<400> SEQUENCE: 7

Met Ser Leu Leu Thr Glu Val Glu Thr Pro Thr Arg Asn Glu Trp Glu
  1               5                  10                  15

Cys Arg Cys Ser Asp Ser Ser Asp Pro Ile Tyr Arg Arg Leu Lys Tyr
                 20                  25                  30

Gly Leu Lys Arg Gly Pro Ser Thr Ala Gly Val Pro Glu Ser Met Arg
             35                  40                  45

Glu Glu Tyr Arg Gln Glu Gln Gln Ser Ala Val Asp Val Asp Asp Gly
 50                  55                  60
```

```
His Phe Val Asn Ile Glu
 65                  70

<210> SEQ ID NO 8
<211> LENGTH: 155
<212> TYPE: PRT
<213> ORGANISM: Avian influenza virus

<400> SEQUENCE: 8

Gly Tyr Ile Cys Ser Gly Val Phe Gly Asp Asn Pro Arg Pro Asn Asp
 1               5                  10                  15

Gly Thr Gly Ser Cys Gly Pro Met Ser Leu Asn Gly Ala Tyr Gly Val
            20                  25                  30

Lys Gly Phe Ser Phe Lys Tyr Gly Asn Gly Val Trp Ile Gly Arg Thr
        35                  40                  45

Lys Ser Thr Asn Ser Arg Ser Gly Phe Glu Met Ile Trp Asp Pro Asn
    50                  55                  60

Gly Trp Thr Gly Thr Asp Ser Ser Phe Ser Val Lys Gln Asp Ile Val
 65                  70                  75                  80

Ala Ile Thr Asp Trp Ser Gly Tyr Ser Gly Ser Phe Val Gln His Pro
                85                  90                  95

Glu Leu Thr Gly Leu Asp Cys Ile Arg Pro Cys Phe Trp Ile Glu Leu
            100                 105                 110

Ile Arg Gly Arg Pro Lys Glu Ser Thr Ile Trp Thr Ser Gly Ser Ser
        115                 120                 125

Ile Ser Phe Cys Gly Val Asn Ser Asp Thr Val Gly Trp Ser Trp Pro
    130                 135                 140

Asp Gly Ala Glu Leu Pro Phe Thr Ile Asp Lys
145                 150                 155

<210> SEQ ID NO 9
<211> LENGTH: 45
<212> TYPE: DNA
<213> ORGANISM: Artificial Sequence
<220> FEATURE:
<223> OTHER INFORMATION: primer for NS1.

<400> SEQUENCE: 9
ggttccaccc tgggtctgga catccgtacc gctacccgtg aaggt            45

<210> SEQ ID NO 10
<211> LENGTH: 45
<212> TYPE: DNA
<213> ORGANISM: Artificial Sequence
<220> FEATURE:
<223> OTHER INFORMATION: primer for NS1.

<400> SEQUENCE: 10
cgtcgtgacc agaaatccct gcgtggtcgt ggttccaccc tgggt            45

<210> SEQ ID NO 11
<211> LENGTH: 49
<212> TYPE: DNA
<213> ORGANISM: Artificial Sequence
<220> FEATURE:
<223> OTHER INFORMATION: primer for NS1.

<400> SEQUENCE: 11
gaactgggtg acgctccgtt cctggaccgt ctgcgtcgtg accagaaaa        49

<210> SEQ ID NO 12
```

```
<211> LENGTH: 48
<212> TYPE: DNA
<213> ORGANISM: Artificial Sequence
<220> FEATURE:
<223> OTHER INFORMATION: primer for NS1.

<400> SEQUENCE: 12
ctgtggcgtg ttcgtaaacg tttcgctgac caggaactgg gtgacgct                    48

<210> SEQ ID NO 13
<211> LENGTH: 46
<212> TYPE: DNA
<213> ORGANISM: Artificial Sequence
<220> FEATURE:
<223> OTHER INFORMATION: primer for NS1.

<400> SEQUENCE: 13
caccgtttcc tccttccagg ttgactgctt cctgtggcgt gttcgt                      46

<210> SEQ ID NO 14
<211> LENGTH: 47
<212> TYPE: DNA
<213> ORGANISM: Artificial Sequence
<220> FEATURE:
<223> OTHER INFORMATION: primer for NS1.

<400> SEQUENCE: 14
cccgaattcc atatggtcga catggactcc aacaccgttt cctcctt                     47

<210> SEQ ID NO 15
<211> LENGTH: 45
<212> TYPE: DNA
<213> ORGANISM: Artificial Sequence
<220> FEATURE:
<223> OTHER INFORMATION: primer for NS1.

<400> SEQUENCE: 15
ttcttccagg atacgttcaa cgatgtgttt accttcacgg gtagc                       45

<210> SEQ ID NO 16
<211> LENGTH: 43
<212> TYPE: DNA
<213> ORGANISM: Artificial Sequence
<220> FEATURE:
<223> OTHER INFORMATION: primer for NS1.

<400> SEQUENCE: 16
ggtcattttc agagcttcgt cggattcttc ttccaggata cgt                         43

<210> SEQ ID NO 17
<211> LENGTH: 43
<212> TYPE: DNA
<213> ORGANISM: Artificial Sequence
<220> FEATURE:
<223> OTHER INFORMATION: primer for NS1.

<400> SEQUENCE: 17
gtaacgcgga gccggaacgg aagcgatggt cattttcaga gct                         43

<210> SEQ ID NO 18
<211> LENGTH: 48
<212> TYPE: DNA
<213> ORGANISM: Artificial Sequence
<220> FEATURE:
<223> OTHER INFORMATION: primer for NS1.

<400> SEQUENCE: 18
```
acgggacatt tcttccaggg tcataccggt caggtaacgc ggagccgg        48

<210> SEQ ID NO 19
<211> LENGTH: 54
<212> TYPE: DNA
<213> ORGANISM: Artificial Sequence
<220> FEATURE:
<223> OTHER INFORMATION: primer for NS1.

<400> SEQUENCE: 19
accggtaact ttctgtttcg ggatcagcat cagccagtca cgggacattt cttc        54

<210> SEQ ID NO 20
<211> LENGTH: 51
<212> TYPE: DNA
<213> ORGANISM: Artificial Sequence
<220> FEATURE:
<223> OTHER INFORMATION: primer for NS1.

<400> SEQUENCE: 20
attatttttc tcgaggtcca tacggatgca cagggaaccg gtaactttct g        51

<210> SEQ ID NO 21
<211> LENGTH: 42
<212> TYPE: DNA
<213> ORGANISM: Artificial Sequence
<220> FEATURE:
<223> OTHER INFORMATION: primer for fragment NA-a.

<400> SEQUENCE: 21
gctaccgaaa tccgtgcttc cgttggtcgt atgatctccg gt        42

<210> SEQ ID NO 22
<211> LENGTH: 45
<212> TYPE: DNA
<213> ORGANISM: Artificial Sequence
<220> FEATURE:
<223> OTHER INFORMATION: primer for fragment NP-a.

<400> SEQUENCE: 22
cagatggaaa ccggtggtga acgtcagaac gctaccgaaa tccgt        45

<210> SEQ ID NO 23
<211> LENGTH: 41
<212> TYPE: DNA
<213> ORGANISM: Artificial Sequence
<220> FEATURE:
<223> OTHER INFORMATION: primer for fragment NP-a.

<400> SEQUENCE: 23
tcccagggta ccaaacgttc ctacgaacag atggaaaccg g        41

<210> SEQ ID NO 24
<211> LENGTH: 43
<212> TYPE: DNA
<213> ORGANISM: Artificial Sequence
<220> FEATURE:
<223> OTHER INFORMATION: primer for fragment NP-a.

<400> SEQUENCE: 24
aaagaattcg tcgaccatat gatggcttcc cagggtacca aac        43

<210> SEQ ID NO 25
<211> LENGTH: 43
<212> TYPE: DNA
<213> ORGANISM: Artificial Sequence
<220> FEATURE:

<223> OTHER INFORMATION: primer for fragment NP-a.

<400> SEQUENCE: 25
gcacatctgg atgtagaaac gaccgatacc ggagatcata cga         43

<210> SEQ ID NO 26
<211> LENGTH: 46
<212> TYPE: DNA
<213> ORGANISM: Artificial Sequence
<220> FEATURE:
<223> OTHER INFORMATION: primer for fragment NP-a.

<400> SEQUENCE: 26
gaccttcgta gtcggacagt ttcagttcgg tgcacatctg gatgta       46

<210> SEQ ID NO 27
<211> LENGTH: 44
<212> TYPE: DNA
<213> ORGANISM: Artificial Sequence
<220> FEATURE:
<223> OTHER INFORMATION: primer for fragment NP-a.

<400> SEQUENCE: 27
ttcgtctttt ttggagttct gcatcagacg accttcgtag tcgg         44

<210> SEQ ID NO 28
<211> LENGTH: 42
<212> TYPE: DNA
<213> ORGANISM: Artificial Sequence
<220> FEATURE:
<223> OTHER INFORMATION: primer for fragment NP-a.

<400> SEQUENCE: 28
gggctcgagt ttcagttcgt cacgcagttc gtctttttg ga           42

<210> SEQ ID NO 29
<211> LENGTH: 41
<212> TYPE: DNA
<213> ORGANISM: Artificial Sequence
<220> FEATURE:
<223> OTHER INFORMATION: primer for fragment NP-b.

<400> SEQUENCE: 29
tgggttcgtg aactgatcct gtacgacaaa gaagaaatcc g           41

<210> SEQ ID NO 30
<211> LENGTH: 41
<212> TYPE: DNA
<213> ORGANISM: Artificial Sequence
<220> FEATURE:
<223> OTHER INFORMATION: primer for fragment NP-b.

<400> SEQUENCE: 30
ccgatctacc gtcgtcgtga cggtaaatgg gttcgtgaac t           41

<210> SEQ ID NO 31
<211> LENGTH: 45
<212> TYPE: DNA
<213> ORGANISM: Artificial Sequence
<220> FEATURE:
<223> OTHER INFORMATION: primer for fragment NP-b.

<400> SEQUENCE: 31
gctggtaaag acccgaaaaa aaccggtggt ccgatctacc gtcgt        45

<210> SEQ ID NO 32

```
<211> LENGTH: 42
<212> TYPE: DNA
<213> ORGANISM: Artificial Sequence
<220> FEATURE:
<223> OTHER INFORMATION: primer for fragment NP-b.

<400> SEQUENCE: 32
aaccgttacc tggaagaaca cccgtccgct ggtaaagacc cg                    42

<210> SEQ ID NO 33
<211> LENGTH: 42
<212> TYPE: DNA
<213> ORGANISM: Artificial Sequence
<220> FEATURE:
<223> OTHER INFORMATION: primer for fragment NP-b.

<400> SEQUENCE: 33
gttctgtccg ctttcgacga acgtcgtaac cgttacctgg aa                    42

<210> SEQ ID NO 34
<211> LENGTH: 42
<212> TYPE: DNA
<213> ORGANISM: Artificial Sequence
<220> FEATURE:
<223> OTHER INFORMATION: primer for fragment NP-b.

<400> SEQUENCE: 34
aaagaattcg tcgaccatat gcgtatggtt ctgtccgctt tc                    42

<210> SEQ ID NO 35
<211> LENGTH: 43
<212> TYPE: DNA
<213> ORGANISM: Artificial Sequence
<220> FEATURE:
<223> OTHER INFORMATION: primer for NP-b.

<400> SEQUENCE: 35
caccgttgtt agcctgacgc cagatacgac ggatttcttc ttt                   43

<210> SEQ ID NO 36
<211> LENGTH: 44
<212> TYPE: DNA
<213> ORGANISM: Artificial Sequence
<220> FEATURE:
<223> OTHER INFORMATION: primer for fragment NP-b.

<400> SEQUENCE: 36
caggtgggtc agaccagcgg tagcgtcttc accgttgtta gcct                  44

<210> SEQ ID NO 37
<211> LENGTH: 41
<212> TYPE: DNA
<213> ORGANISM: Artificial Sequence
<220> FEATURE:
<223> OTHER INFORMATION: primer for fragment NP-b.

<400> SEQUENCE: 37
tcgttcaggt tggagtgcca gatcatcagg tgggtcagac c                     41

<210> SEQ ID NO 38
<211> LENGTH: 42
<212> TYPE: DNA
<213> ORGANISM: Artificial Sequence
<220> FEATURE:
<223> OTHER INFORMATION: primer for fragment NP-b.

<400> SEQUENCE: 38
```
cacagcacgg gtacgctggt aggtagcgtc gttcaggttg ga                                          42

<210> SEQ ID NO 39
<211> LENGTH: 46
<212> TYPE: DNA
<213> ORGANISM: Artificial Sequence
<220> FEATURE:
<223> OTHER INFORMATION: primer for fragment NP-b.

<400> SEQUENCE: 39
agcacatacg cgggtccata ccggtacgaa ccagagcacg ggtacg                                      46

<210> SEQ ID NO 40
<211> LENGTH: 44
<212> TYPE: DNA
<213> ORGANISM: Artificial Sequence
<220> FEATURE:
<223> OTHER INFORMATION: primer for fragment NP-b.

<400> SEQUENCE: 40
gggctcgagt ttcagttcgt cttttttgga gcacatacgc gggt                                        44

<210> SEQ ID NO 41
<211> LENGTH: 44
<212> TYPE: DNA
<213> ORGANISM: Artificial Sequence
<220> FEATURE:
<223> OTHER INFORMATION: primer for fragment NP-c.

<400> SEQUENCE: 41
ctgaaaggta aattccagac cgctgctcag cgtgctatga tgga                                        44

<210> SEQ ID NO 42
<211> LENGTH: 42
<212> TYPE: DNA
<213> ORGANISM: Artificial Sequence
<220> FEATURE:
<223> OTHER INFORMATION: primer for fragment NP-c.

<400> SEQUENCE: 42
atcgcttacg aacgtatgtg caacatcctg aaaggtaaat tc                                          42

<210> SEQ ID NO 43
<211> LENGTH: 42
<212> TYPE: DNA
<213> ORGANISM: Artificial Sequence
<220> FEATURE:
<223> OTHER INFORMATION: primer for fragment NP-c.

<400> SEQUENCE: 43
cgtggtgaaa acggtcgtcg tacccgtatc gcttacgaac gt                                          42

<210> SEQ ID NO 44
<211> LENGTH: 42
<212> TYPE: DNA
<213> ORGANISM: Artificial Sequence
<220> FEATURE:
<223> OTHER INFORMATION: primer for fragment NP-c.

<400> SEQUENCE: 44
cgtggtatcg acgaccgtaa cttctggcgt ggtgaaaacg gt                                          42

<210> SEQ ID NO 45
<211> LENGTH: 41
<212> TYPE: DNA
<213> ORGANISM: Artificial Sequence
<220> FEATURE:

```
<223> OTHER INFORMATION: primer for fragment NP-c.

<400> SEQUENCE: 45
gttatggaac tgatccgtat gatcaaacgt ggtatcgacg a                    41

<210> SEQ ID NO 46
<211> LENGTH: 41
<212> TYPE: DNA
<213> ORGANISM: Artificial Sequence
<220> FEATURE:
<223> OTHER INFORMATION: primer for fragment NP-c.

<400> SEQUENCE: 46
gctgctgtta aaggtgttgg taccatggtt atggaactga t                    41

<210> SEQ ID NO 47
<211> LENGTH: 42
<212> TYPE: DNA
<213> ORGANISM: Artificial Sequence
<220> FEATURE:
<223> OTHER INFORMATION: primer for fragment NP-c.

<400> SEQUENCE: 47
ctgccgcgtc gttccggtgc tgctggtgct gctgttaaag gt                   42

<210> SEQ ID NO 48
<211> LENGTH: 39
<212> TYPE: DNA
<213> ORGANISM: Artificial Sequence
<220> FEATURE:
<223> OTHER INFORMATION: primer for fragment NP-c.

<400> SEQUENCE: 48
aaagaattcg tcgaccatta gaccctgccg cgtcgttcc                       39

<210> SEQ ID NO 49
<211> LENGTH: 45
<212> TYPE: DNA
<213> ORGANISM: Artificial Sequence
<220> FEATURE:
<223> OTHER INFORMATION: primer for fragment NP-c.

<400> SEQUENCE: 49
agccaggaag atcagcagtt cgtctttttt gtccatcata gcacg                45

<210> SEQ ID NO 50
<211> LENGTH: 41
<212> TYPE: DNA
<213> ORGANISM: Artificial Sequence
<220> FEATURE:
<223> OTHER INFORMATION: primer for fragment NP-c.

<400> SEQUENCE: 50
ggaaccacgc aggatcagag cggaacgagc caggaagatc a                    41

<210> SEQ ID NO 51
<211> LENGTH: 43
<212> TYPE: DNA
<213> ORGANISM: Artificial Sequence
<220> FEATURE:
<223> OTHER INFORMATION: primer for fragment NP-c.

<400> SEQUENCE: 51
agccggcagg caggatttgt gagcaacgga accacgcagg atc                  43

<210> SEQ ID NO 52
```

```
<211> LENGTH: 42
<212> TYPE: DNA
<213> ORGANISM: Artificial Sequence
<220> FEATURE:
<223> OTHER INFORMATION: primer for fragment NP-c.

<400> SEQUENCE: 52
ggaagcaaca gccagaccgt aaacgcaagc cggcaggcag ga                               42

<210> SEQ ID NO 53
<211> LENGTH: 41
<212> TYPE: DNA
<213> ORGANISM: Artificial Sequence
<220> FEATURE:
<223> OTHER INFORMATION: primer for fragment NP-c.

<400> SEQUENCE: 53
gtaaccttca cgttcgaagt cgtaaccgga agcaacagcc a                                41

<210> SEQ ID NO 54
<211> LENGTH: 42
<212> TYPE: DNA
<213> ORGANISM: Artificial Sequence
<220> FEATURE:
<223> OTHER INFORMATION: primer for fragment NP-c.

<400> SEQUENCE: 54
acggaacggg tcgataccaa ccagggagta accttcacgt tc                               42

<210> SEQ ID NO 55
<211> LENGTH: 42
<212> TYPE: DNA
<213> ORGANISM: Artificial Sequence
<220> FEATURE:
<223> OTHER INFORMATION: primer for fragment NP-c.

<400> SEQUENCE: 55
ggagaaaacc tgggagtttt gcagcagacg gaacgggtcg at                               42

<210> SEQ ID NO 56
<211> LENGTH: 42
<212> TYPE: DNA
<213> ORGANISM: Artificial Sequence
<220> FEATURE:
<223> OTHER INFORMATION: primer for fragment NP-c.

<400> SEQUENCE: 56
gggctcgagt ttcagttcgt cacgcaggga gaaaacctgg ga                               42

<210> SEQ ID NO 57
<211> LENGTH: 41
<212> TYPE: DNA
<213> ORGANISM: Artificial Sequence
<220> FEATURE:
<223> OTHER INFORMATION: primer for fragment NP-d.

<400> SEQUENCE: 57
cgtaacctgc cgttcgaacg tgctaccatc atggctgttt t                                41

<210> SEQ ID NO 58
<211> LENGTH: 41
<212> TYPE: DNA
<213> ORGANISM: Artificial Sequence
<220> FEATURE:
<223> OTHER INFORMATION: primer for fragment NP-d.

<400> SEQUENCE: 58
```

```
gaagacaaaa aaaccttctc cgttcagcgt aacctgccgt t              41
```

<210> SEQ ID NO 59
<211> LENGTH: 46
<212> TYPE: DNA
<213> ORGANISM: Artificial Sequence
<220> FEATURE:
<223> OTHER INFORMATION: primer for fragment NP-d.

<400> SEQUENCE: 59

```
gctatccgta cccgttccgg tggtaacctg aagacaaaa aaacct         46
```

<210> SEQ ID NO 60
<211> LENGTH: 41
<212> TYPE: DNA
<213> ORGANISM: Artificial Sequence
<220> FEATURE:
<223> OTHER INFORMATION: primer for fragment NP-d.

<400> SEQUENCE: 60

```
accctggaac tgcgttcccg ttactccgct atccgtaccc g              41
```

<210> SEQ ID NO 61
<211> LENGTH: 42
<212> TYPE: DNA
<213> ORGANISM: Artificial Sequence
<220> FEATURE:
<223> OTHER INFORMATION: primer for fragment NP-d.

<400> SEQUENCE: 61

```
gaaaacatgg aagctatgga ctccaacacc ctggaactgc gt            42
```

<210> SEQ ID NO 62
<211> LENGTH: 44
<212> TYPE: DNA
<213> ORGANISM: Artificial Sequence
<220> FEATURE:
<223> OTHER INFORMATION: primer for fragment NP-d.

<400> SEQUENCE: 62

```
tccacccgtg gtgttcagat cgcttccaac gaaaacatgg aagc          44
```

<210> SEQ ID NO 63
<211> LENGTH: 45
<212> TYPE: DNA
<213> ORGANISM: Artificial Sequence
<220> FEATURE:
<223> OTHER INFORMATION: primer for fragment NP-d.

<400> SEQUENCE: 63

```
ggtacccgtg ttgttccgcg tggtcagctg tccacccgtg gtgtt         45
```

<210> SEQ ID NO 64
<211> LENGTH: 46
<212> TYPE: DNA
<213> ORGANISM: Artificial Sequence
<220> FEATURE:
<223> OTHER INFORMATION: primer for fragment NP-d.

<400> SEQUENCE: 64

```
aaagaattcg tcgaccatat gttcatccgt ggtacccgtg ttgttc        46
```

<210> SEQ ID NO 65
<211> LENGTH: 42
<212> TYPE: DNA
<213> ORGANISM: Artificial Sequence
<220> FEATURE:

<223> OTHER INFORMATION: primer for fragment NP-d.

<400> SEQUENCE: 65
ggaggtacga ccttcggtgt taccggtgaa aacagccatg at                               42

<210> SEQ ID NO 66
<211> LENGTH: 44
<212> TYPE: DNA
<213> ORGANISM: Artificial Sequence
<220> FEATURE:
<223> OTHER INFORMATION: primer for fragment NP-d.

<400> SEQUENCE: 66
catcatacgg atgatttcgg tacgcatgtc ggaggtacga cctt                             44

<210> SEQ ID NO 67
<211> LENGTH: 45
<212> TYPE: DNA
<213> ORGANISM: Artificial Sequence
<220> FEATURE:
<223> OTHER INFORMATION: rimer for fragment NP-d.

<400> SEQUENCE: 67
gaaggaaacg tcttccggac gagcggattc catcatacgg atgat                            45

<210> SEQ ID NO 68
<211> LENGTH: 44
<212> TYPE: DNA
<213> ORGANISM: Artificial Sequence
<220> FEATURE:
<223> OTHER INFORMATION: primer for fragment NP-d.

<400> SEQUENCE: 68
gtcggacagt tcgaaaacac cacgaccctg gaaggaaacg tctt                             44

<210> SEQ ID NO 69
<211> LENGTH: 45
<212> TYPE: DNA
<213> ORGANISM: Artificial Sequence
<220> FEATURE:
<223> OTHER INFORMATION: primer for fragment NP-d.

<400> SEQUENCE: 69
ggacggaacg atcggttgg tagcttttc gtcggacagt tcgaa                              45

<210> SEQ ID NO 70
<211> LENGTH: 41
<212> TYPE: DNA
<213> ORGANISM: Artificial Sequence
<220> FEATURE:
<223> OTHER INFORMATION: primer for fragment NP-d.

<400> SEQUENCE: 70
taggaacctt cgttgttcat gtcgaaggac ggaacgatcg g                                41

<210> SEQ ID NO 71
<211> LENGTH: 42
<212> TYPE: DNA
<213> ORGANISM: Artificial Sequence
<220> FEATURE:
<223> OTHER INFORMATION: primer for fragment NP-d.

<400> SEQUENCE: 71
gtattcttca gcgttgtcac cgaagaagta ggaaccttcg tt                               42

<210> SEQ ID NO 72

```
<211> LENGTH: 45
<212> TYPE: DNA
<213> ORGANISM: Artificial Sequence
<220> FEATURE:
<223> OTHER INFORMATION: primer for fragment NP-d.

<400> SEQUENCE: 72
gggctcgagt tcagttcgt cacggttgta gtattcttca gcgtt                45

<210> SEQ ID NO 73
<211> LENGTH: 45
<212> TYPE: DNA
<213> ORGANISM: Artificial Sequence
<220> FEATURE:
<223> OTHER INFORMATION: primer for fragment HA.

<400> SEQUENCE: 73
gttgtttggc tgatcaagaa aaacaacgct tacccgacca tcaaa                45

<210> SEQ ID NO 74
<211> LENGTH: 45
<212> TYPE: DNA
<213> ORGANISM: Artificial Sequence
<220> FEATURE:
<223> OTHER INFORMATION: primer for fragment HA.

<400> SEQUENCE: 74
tacctgggta atcctccctt cttccgtaac gttgtttggc tgatc                45

<210> SEQ ID NO 75
<211> LENGTH: 46
<212> TYPE: DNA
<213> ORGANISM: Artificial Sequence
<220> FEATURE:
<223> OTHER INFORMATION: primer for fragment HA.

<400> SEQUENCE: 75
agcttcctcc ggtgtttctt ctgcttgccc gtacctgggt aaatcc               46

<210> SEQ ID NO 76
<211> LENGTH: 42
<212> TYPE: DNA
<213> ORGANISM: Artificial Sequence
<220> FEATURE:
<223> OTHER INFORMATION: primer for fragment HA.

<400> SEQUENCE: 76
ccgaaatctt cctggtctaa ccacgaagct tcctccggtg tt                   42

<210> SEQ ID NO 77
<211> LENGTH: 45
<212> TYPE: DNA
<213> ORGANISM: Artificial Sequence
<220> FEATURE:
<223> OTHER INFORMATION: primer for fragment HA.

<400> SEQUENCE: 77
atcaaccact tcgaaaaaat ccagatcatc ccgaaatctt cctgg                45

<210> SEQ ID NO 78
<211> LENGTH: 46
<212> TYPE: DNA
<213> ORGANISM: Artificial Sequence
<220> FEATURE:
<223> OTHER INFORMATION: primer for fragment HA.

<400> SEQUENCE: 78
```

-continued ctacgaagaa ctgaaacacc tgctgtcccg tatcaaccac ttcgaa     46

<210> SEQ ID NO 79
<211> LENGTH: 42
<212> TYPE: DNA
<213> ORGANISM: Artificial Sequence
<220> FEATURE:
<223> OTHER INFORMATION: primer for fragment HA.

<400> SEQUENCE: 79
ctgtgctacc cgggtgactt caacgactac gaagaactga aa     42

<210> SEQ ID NO 80
<211> LENGTH: 45
<212> TYPE: DNA
<213> ORGANISM: Artificial Sequence
<220> FEATURE:
<223> OTHER INFORMATION: primer for fragment HA.

<400> SEQUENCE: 80
cccgaattcc atatggtcga cgctaacgac ctgtgctacc cgggt     45

<210> SEQ ID NO 81
<211> LENGTH: 45
<212> TYPE: DNA
<213> ORGANISM: Artificial Sequence
<220> FEATURE:
<223> OTHER INFORMATION: primer for fragment HA.

<400> SEQUENCE: 81
gtcttcctgg ttggtgttgt tgtaggaacg tttgatggtc gggta     45

<210> SEQ ID NO 82
<211> LENGTH: 45
<212> TYPE: DNA
<213> ORGANISM: Artificial Sequence
<220> FEATURE:
<223> OTHER INFORMATION: primer for fragment HA.

<400> SEQUENCE: 82
cgggtggtgg atacccccaca gaaccagcag gtcttcctgg ttggt     45

<210> SEQ ID NO 83
<211> LENGTH: 44
<212> TYPE: DNA
<213> ORGANISM: Artificial Sequence
<220> FEATURE:
<223> OTHER INFORMATION: primer for fragment HA.

<400> SEQUENCE: 83
tacagtttgg tctgttcagc agcgtcgttc gggtggtgga tacc     44

<210> SEQ ID NO 84
<211> LENGTH: 48
<212> TYPE: DNA
<213> ORGANISM: Artificial Sequence
<220> FEATURE:
<223> OTHER INFORMATION: primer for fragment HA.

<400> SEQUENCE: 84
accaacggag atgtaggtgg tcgggttctg gtacagtttg gtctgttc     48

<210> SEQ ID NO 85
<211> LENGTH: 45
<212> TYPE: DNA
<213> ORGANISM: Artificial Sequence
<220> FEATURE:

<223> OTHER INFORMATION: primer for fragment HA.

<400> SEQUENCE: 85
cggaaccaga cgctggttca gggtggaggt accaacggag atgta    45

<210> SEQ ID NO 86
<211> LENGTH: 45
<212> TYPE: DNA
<213> ORGANISM: Artificial Sequence
<220> FEATURE:
<223> OTHER INFORMATION: primer for fragment HA.

<400> SEQUENCE: 86
accgttaact ttggaacggg tagcgatttt cggaaccaga cgctg    45

<210> SEQ ID NO 87
<211> LENGTH: 45
<212> TYPE: DNA
<213> ORGANISM: Artificial Sequence
<220> FEATURE:
<223> OTHER INFORMATION: primer for fragment HA.

<400> SEQUENCE: 87
ggtccagaag aactccatac gaccggactg accgttaact ttgga    45

<210> SEQ ID NO 88
<211> LENGTH: 42
<212> TYPE: DNA
<213> ORGANISM: Artificial Sequence
<220> FEATURE:
<223> OTHER INFORMATION: primer for fragment HA.

<400> SEQUENCE: 88 attattttc tcgagcggtt tcaggatggt ccagaagaac tc    42

<210> SEQ ID NO 89
<211> LENGTH: 21
<212> TYPE: DNA
<213> ORGANISM: Artificial Sequence
<220> FEATURE:
<223> OTHER INFORMATION: primer for fragment M2.

<400> SEQUENCE: 89
atctaccgtc gtctgaaata c    21

<210> SEQ ID NO 90
<211> LENGTH: 42
<212> TYPE: DNA
<213> ORGANISM: Artificial
<220> FEATURE:
<223> OTHER INFORMATION: primer for fragment M2.

<400> SEQUENCE: 90
tgccgttgca gcgacagcag cgacccgatc taccgtcgtc tg    42

<210> SEQ ID NO 91
<211> LENGTH: 39
<212> TYPE: DNA
<213> ORGANISM: Artificial Sequence
<220> FEATURE:
<223> OTHER INFORMATION: primer for fragment M2.

<400> SEQUENCE: 91
ccccgacccg taacgaatgg gaatgccgtt gcagcgaca    39

<210> SEQ ID NO 92

<211> LENGTH: 66
<212> TYPE: DNA
<213> ORGANISM: Artificial Sequence
<220> FEATURE:
<223> OTHER INFORMATION: primer for fragment M2.

<400> SEQUENCE: 92
aaaaagaatt cgtcgaccat atgagcctgc tgaccgaagt tgaaacccg acccgtaacg    60 aattgg    66

<210> SEQ ID NO 93
<211> LENGTH: 54
<212> TYPE: DNA
<213> ORGANISM: Artificial Sequence
<220> FEATURE:
<223> OTHER INFORMATION: primer for fragment M2.

<400> SEQUENCE: 93
tttcagaccg tatttcagac gacggtagat gcatttgaag aacagacggt ccag    54

<210> SEQ ID NO 94
<211> LENGTH: 52
<212> TYPE: DNA
<213> ORGANISM: Artificial Sequence
<220> FEATURE:
<223> OTHER INFORMATION: primer for fragment M2.

<400> SEQUENCE: 94
gcatgctttc cggaacacca gcggtgctcg gaccacgttt cagaccgtat tt    52

<210> SEQ ID NO 95
<211> LENGTH: 51
<212> TYPE: DNA
<213> ORGANISM: Artificial Sequence
<220> FEATURE:
<223> OTHER INFORMATION: primer for fragment M2.

<400> SEQUENCE: 95
agcgctctgc tgttcctgac ggtattcttc acgcatgctt tccggaacac c    51

<210> SEQ ID NO 96
<211> LENGTH: 67
<212> TYPE: DNA
<213> ORGANISM: Artificial Sequence
<220> FEATURE:
<223> OTHER INFORMATION: primer for fragment M2.

<400> SEQUENCE: 96
tttctcgagt tcgatgttaa cgaagtgacc gtcgtcaacg tcaacagcgc tctgctgttc    60
ctgacgg    67

<210> SEQ ID NO 97
<211> LENGTH: 47
<212> TYPE: DNA
<213> ORGANISM: Artificial Sequence
<220> FEATURE:
<223> OTHER INFORMATION: primer for fragment NA.

<400> SEQUENCE: 97
ggttggaccg gtaccgactc ctccttctcc gttaaacagg acatcgt    47

<210> SEQ ID NO 98
<211> LENGTH: 45
<212> TYPE: DNA
<213> ORGANISM: Artificial Sequence
<220> FEATURE:

<223> OTHER INFORMATION: primer for fragment NA.

<400> SEQUENCE: 98
tccggtttcg aaatgatctg ggacccgaac ggttggaccg gtacc    45

<210> SEQ ID NO 99
<211> LENGTH: 45
<212> TYPE: DNA
<213> ORGANISM: Artificial Sequence
<220> FEATURE:
<223> OTHER INFORMATION: primer for fragment NA.

<400> SEQUENCE: 99
atcggtcgta ccaaatccac caactcccgt tccggtttcg aaatg    45

<210> SEQ ID NO 100
<211> LENGTH: 47
<212> TYPE: DNA
<213> ORGANISM: Artificial Sequence
<220> FEATURE:
<223> OTHER INFORMATION: primer for fragment NA.

<400> SEQUENCE: 100
gtttctcctt caaatacggt aacggtgttt ggatcggtcg taccaaa    47

<210> SEQ ID NO 101
<211> LENGTH: 48
<212> TYPE: DNA
<213> ORGANISM: Artificial Sequence
<220> FEATURE:
<223> OTHER INFORMATION: primer for fragment NA.

<400> SEQUENCE: 101
atgtccctga acggtgctta cggtgttaaa ggtttctcct tcaaatac    48

<210> SEQ ID NO 102
<211> LENGTH: 45
<212> TYPE: DNA
<213> ORGANISM: Artificial Sequence
<220> FEATURE:
<223> OTHER INFORMATION: primer for fragment NA.

<400> SEQUENCE: 102
ccgaacgacg gtaccggttc ctgcggtccg atgtccctga acggt    45

<210> SEQ ID NO 103
<211> LENGTH: 45
<212> TYPE: DNA
<213> ORGANISM: Artificial Sequence
<220> FEATURE:
<223> OTHER INFORMATION: primer for fragment NA.

<400> SEQUENCE: 103
tgctccggtg ttttcggtga caacccgcgt ccgaacgacg gtacc    45

<210> SEQ ID NO 104
<211> LENGTH: 48
<212> TYPE: DNA
<213> ORGANISM: Artificial Sequence
<220> FEATURE:
<223> OTHER INFORMATION: primer for fragment NA.

<400> SEQUENCE: 104
cccgaattcc atatggtcga cggttacatc tgctccggtg ttttcggt    48

<210> SEQ ID NO 105

-continued

```
<211> LENGTH: 48
<212> TYPE: DNA
<213> ORGANISM: Artificial Sequence
<220> FEATURE:
<223> OTHER INFORMATION: primer for fragment NA.

<400> SEQUENCE: 105
accggagtaa ccggaccagt cggtgatagc aacgatgtcc tgtttaac        48

<210> SEQ ID NO 106
<211> LENGTH: 46
<212> TYPE: DNA
<213> ORGANISM: Artificial Sequence
<220> FEATURE:
<223> OTHER INFORMATION: primer for fragment NA.

<400> SEQUENCE: 106
gaccggtcag ttccgggtgc tgaacgaagg aaccggagta accgga           46

<210> SEQ ID NO 107
<211> LENGTH: 48
<212> TYPE: DNA
<213> ORGANISM: Artificial Sequence
<220> FEATURE:
<223> OTHER INFORMATION: primer for fragment NA.

<400> SEQUENCE: 107
ttcgatccag aagcacggac ggatgcagtc cagaccggtc agttccgg         48

<210> SEQ ID NO 108
<211> LENGTH: 45
<212> TYPE: DNA
<213> ORGANISM: Artificial Sequence
<220> FEATURE:
<223> OTHER INFORMATION: primer for fragment NA.

<400> SEQUENCE: 108
ggtggattct ttcggacgac cacggatcag ttcgatccag aagca            45

<210> SEQ ID NO 109
<211> LENGTH: 46
<212> TYPE: DNA
<213> ORGANISM: Artificial Sequence
<220> FEATURE:
<223> OTHER INFORMATION: primer for fragment NA.

<400> SEQUENCE: 109
agaaggagat ggaggaaccg gaggtccaga tggtggattc tttcgg           46

<210> SEQ ID NO 110
<211> LENGTH: 12
<212> TYPE: PRT
<213> ORGANISM: Artificial Sequence
<220> FEATURE:
<223> OTHER INFORMATION: a carboxyl terminal moiety sequence of PRRSV
      fusion antigens

<400> SEQUENCE: 110

Lys Lys Asp Leu Arg Asp Glu Leu Lys Asp Glu Leu
1               5                   10

<210> SEQ ID NO 111
<211> LENGTH: 13
<212> TYPE: PRT
<213> ORGANISM: Artificial Sequence
<220> FEATURE:
<223> OTHER INFORMATION: a carboxyl terminal moiety sequence of PRRSV
      fusion antigens
```

-continued

```
<400> SEQUENCE: 111

Lys Lys Asp Glu Leu Arg Asp Glu Leu Lys Asp Glu Leu
1               5                   10

<210> SEQ ID NO 112
<211> LENGTH: 13
<212> TYPE: PRT
<213> ORGANISM: Artificial Sequence
<220> FEATURE:
<223> OTHER INFORMATION: a carboxyl terminal moiety sequence of PRRSV
      fusion antigens

<400> SEQUENCE: 112

Lys Lys Asp Glu Leu Arg Val Glu Leu Lys Asp Glu Leu
1               5                   10
```

FUSION ANTIGEN USED AS VACCINE AND METHOD OF MAKING THEM

CROSS-REFERENCE TO RELATED PATENT APPLICATION

This application is a continuation-in-part application, and claims the benefit of U.S. patent application Ser. No. 11/948,327, filed Nov. 30, 2007, issued on Sep. 29, 2009 as U.S. Pat. No. 7,595,054, which is a continuation-in-part application and claims the benefit of U.S. patent application Ser. No. 10/457,574, filed Jun. 9, 2003, issued on Feb. 26, 2008 as U.S. Pat. No. 7,335,361, all of which is herein incorporated by reference in its entireties.

FIELD OF THE INVENTION

The invention relates to a fusion antigen. More particularly, the invention relates to a fusion antigen used as vaccine and methods of making the same.

BACKGROUND OF THE INVENTION

To generate a vaccine, a pathogen must be rendered harmless but still contain sufficient antigenic information to allow virulent wild-type pathogens to be recognized by the immune system. Attenuation of viruses is a tedious, somewhat haphazard, process which greatly slows down the process of developing vaccines. The researchers involved in manipulating the pathogens are also at risk of infection, even with stringent containment protocols. There is an urgent need to speed up the process of vaccine production. Viruses such as influenza are jumping back and forth between humans and animals, mutating slightly as they change hosts. Some of these species transitions have caused pandemics, such as the avian to human jump in 1918 of Influenza A (H1N1) that killed between 20 and 100 million people worldwide. Such a large reservoir of rapidly changing viruses makes it difficult for the medical community to keep ahead of the need to protect humans and animals against disease agents.

Molecular biological techniques have been used to speed up the process of vaccine development and to make them safer. Recombinant vectors containing genes encoding structural proteins HA and NA of H3N2, H6N1, and H9N2, and vectors containing genes encoding PA, PB1, PB2, NP, and M were used to generate a novel vaccinal strain. Immunological studies have indicated that as few as 6 to 8 amino acid residues are needed to generate an antigenic determinant. Combination of antigens with favorable characteristics such as the ability to neutralize viruses with vector systems that enhance their recognition by the immune system also has the potential to rapidly create superior vaccines which are safer than ones made attenuated viruses.

A previously unaddressed need exists in the art to address the aforementioned deficiencies and inadequacies, especially in connection with development of T-cell vaccines against virus infection.

SUMMARY OF THE INVENTION

The invention is related to fusion antigen used as vaccine and method of making them. In one aspect, the method includes: (1) selecting a segment of a virus protein sequence that contains a least one epitope; (2) engineering a DNA fragment encoding the selected segment of the virus protein; (3) inserting the DNA fragment into a *Pseudomonas* Exotoxin A (PE) vector to obtain a chimeric gene plasmid, and expressing the chimeric gene plasmid in a host cell to obtain the chimeric vaccinal virus antigen. The PE vector contains a PE fragment, which has a binding domain and a translocation domain, and a carboxyl terminal moiety, which includes an endoplasmic reticulum (ER) retention sequence. The DNA fragment encoding the selected segment of the virus protein is inserted between the PE fragment and the carboxyl terminal moiety. The chimeric vaccinal virus antigen obtained from the method has a selected virus protein sequence that is not located within any PE domain loops.

In another aspect, the method makes a chimeric vaccinal virus antigen that has all the same steps as aforementioned except the step (3), in which the DNA fragment is inserted into a *Pseudomonas* Exotoxin A (PE) vector that does not contain an ER retention sequence at the carboxyl terminal moiety. Thus, the resulted chimeric vaccinal virus antigen does not present an ER retention sequence.

BRIEF DESCRIPTION OF THE DRAWINGS

FIG. 4 shows lung section histochemistry from ICR mice 14 days post challenge with H5N2 type virus.

DETAILED DESCRIPTION OF THE INVENTION

Definitions

Figure 1:
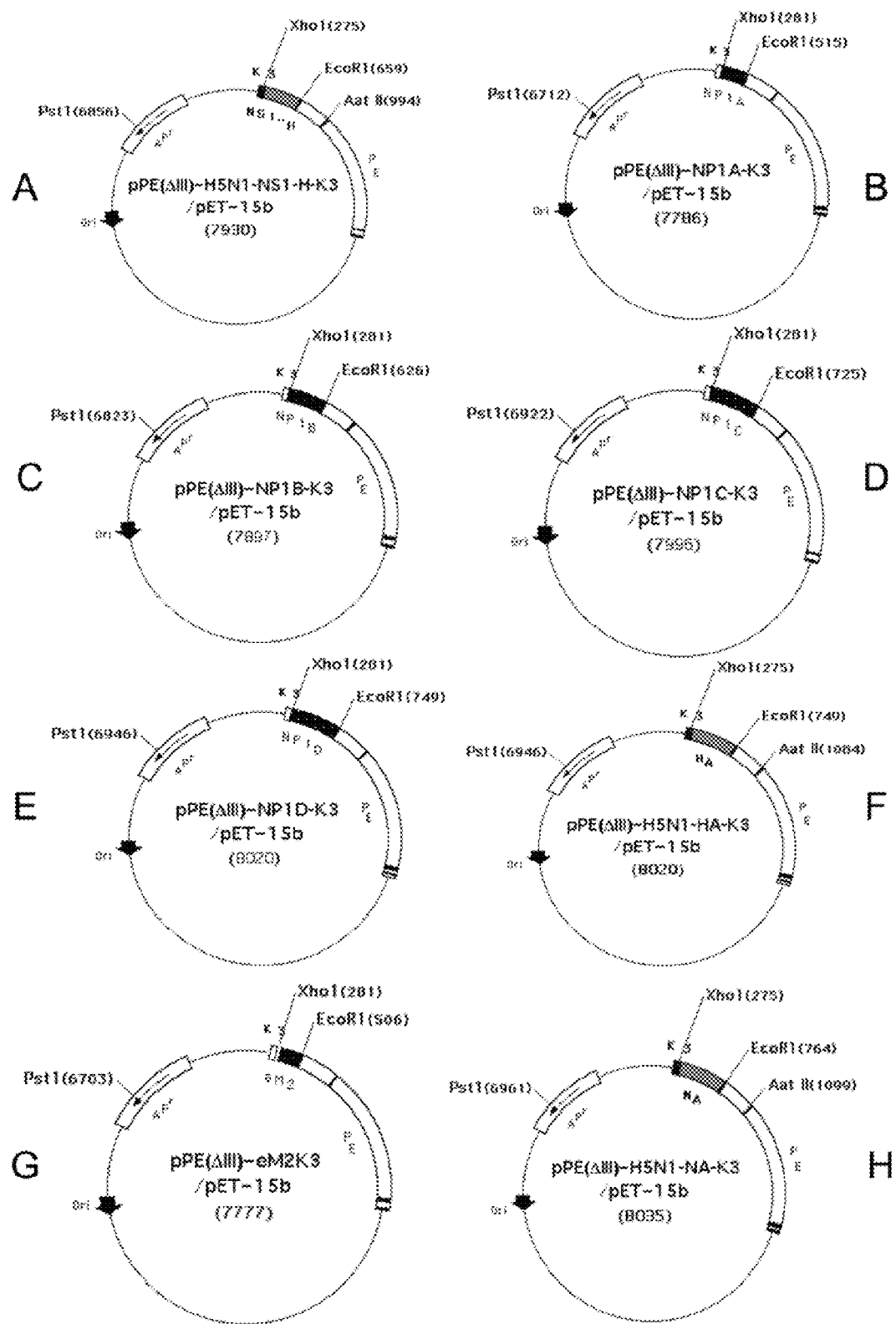
FIGS. 1A-1H are plasmid maps.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The invention provides a fusion antigen specific for a target cell comprising an antigenic moiety, a ligand moiety which is capable of reacting, recognizing or binding to a receptor on the target cell, a *Pseudomonas* exotoxin A translocation domain II, and a carboxyl terminal moiety which permits retention of the fusion antigen in the ER membrane of the target cell.

As used herein, the term "fusion antigen" refers to a recombinant protein which can evoke an immune response in an animal. Preferably, the fusion antigen comprises epitopes for evoking an immune response directly and other portions for enhancing an immune response such as mediating delivery, transporting, processing, and expressing or for equipment of multiple functions.

Preferably, the target cell is an antigen presenting cell. More preferably, the target cell is selected from the group consisting of T-cells, B-cells, dendritic cells, monocytes, and macrophages.

As used herein, the term "an antigenic moiety" refers to a peptide fragment that can evoke an immune response. In one embodiment of the invention, the antigenic moiety is an epitope. According to the invention, the antigenic moiety is a protein of a pathogenic species, which can highly activate an immune response. Such proteins comprise, for example, but are not limited to, coat proteins, nucleoproteins or cell membrane proteins. The antigenic moiety can be a peptide cloned directly from the pathogenic species as well as a recombinant protein modified by artisans skilled in the field for enhancing the ability to evoke an immune response, for being manufactured more conveniently and for being delivered more easily. For evoking a more severe immune response, the antigenic moiety comprises at least one antigenic unit and the adjacent antigenic unit is connected by a bridge region. According to the invention, the bridge region may be a small fragment of peptide that evokes little immune response to prevent the immune system from recognizing it.

As used herein, the term "ligand moiety" refers generally to all molecules which are capable of reacting, recognizing or binding to the receptor on a target cell. Examples of such receptors include, but are not limited to, antibody receptors, growth factor receptors, lymphokine receptors, cytokine receptors, hormone receptors and the like. In some embodiments of the invention, the receptor for binding to the ligand moiety is selected from the group consisting of TGFα receptors, IL2 receptors, IL4 receptors, IL6 receptors, IGF 1 receptors, CD4 receptors, IL18 receptors, IL 12 receptors, EGF receptors, LDL receptors and α2-macroglobulin receptors. The ligand moiety has an ability of binding to the cell membrane of the target cell for anchoring the fusion antigen to the target cell. The immune system is initiated by the fusion antigen's binding to the receptors on the target cell. Preferably, the ligand moiety is a *Pseudomonas* exotoxin A binding domain I. *Pseudomonas* exotoxin A (PE) is a single polypeptide chain of 613 amino acids. PE consists of three domains: an amino terminal cell receptor binding domain (Domain I); a middle translocation domain (Domain II); and a carboxyl terminal activity domain (Domain III) (see U.S. Pat. No. 5,705,163, which is incorporated herein by reference in its entirety).

As used herein, the term "*Pseudomonas* exotoxin A binding domain I" refers to a peptide fragment that has the same sequence as the amino terminal cell receptor binding domain of *Pseudomonas* exotoxin A or a functionally equivalent fragment. The amino terminal cell receptor binding domain of *Pseudomonas* exotoxin A comprises two sub-domains, designated as domain Ia and domain Ib. The configuration of domain Ia and domain Ib can bind to a LDL receptor or a2-macroglobulin receptor on a cell surface.

As used herein, the term "*Pseudomonas* exotoxin A binding domain II" refers to a peptide fragment that has the same sequence as the middle translocation domain of *Pseudomonas* exotoxin A or a functionally equivalent fragment. The *Pseudomonas* exotoxin A translocation domain II has an ability to translocate the fusion antigen into the cytoplasm of the target cell. The fusion antigen is translocated into the target cell after attaching to the target cell membrane.

As used herein, the term "carboxyl terminal moiety which permits retention of the fusion antigen to the endoplasmic reticulum (ER) membrane of a target cell" refers to a peptide fragment that enables the fusion antigen to bind to the ER membrane and to retain it in the ER lumen for glycosylation and make it appears to be more like foreign protein. In one embodiment of the invention, the carboxyl terminal moiety comprises, in a direction from the amino terminus to the carboxyl terminus, the following amino acid residues:

$$R^1-R^2-R^3-R^4-(R^5)_n$$

Wherein,
$R^1$ is a positively charged amino acid residue;
$R^2$ is a negatively charged amino acid residue;
$R^3$ is a negatively charged amino acid residue;
$R^4$ is L;
$R^5$ is a positively charged amino acid residue; and
n is 0 or 1.

Preferably, the carboxyl terminal moiety is a member of the KDEL family protein. As used herein, the term "KDEL family protein" refers to a group of proteins, which has a similar carboxyl end binding to the ER membrane of a cell and further has an ability for retention of such protein in the ER lumen. Generally, the length of the carboxyl end ranges from 4 to 16 residues. As discussed in U.S. Pat. No. 5,705,163 (which is incorporated into the references), the amino residues at the carboxyl end of a KDEL family protein, particularly those in the last five amino acids, are important. As shown in the studies on the similar sequences present in different molecules and performing a specific biological function, a sequence that retains a newly formed protein within the ER is Lys Asp Glu Leu (KDEL). These findings suggest that the sequence at the carboxyl end of the fusion antigen according to the invention acts as some type of recognition sequence to assist translocation of the fusion antigen from an endocytic compartment into the ER and retains it in the lumen. In a preferred embodiment, the carboxyl terminal moiety comprises a sequence of KDEL. In a more preferred embodiment, the carboxyl terminal moiety comprises a sequence of KKDL-RDEL-KDEL (SEQ ID NO: 110), KKDELRDELKDEL (SEQ ID NO: 111), or KKDEL-RVELKDEL (SEQ ID NO: 112), or KKDEL-RXEL-KDEL, in which R is D or V.

The invention is characterized by the design of carboxyl terminal moiety, which enables the fusion antigen to be processed in the ER of the target cell for combining with MHC class I molecules and being recognized by T-cells. The fusion antigen according to the invention is useful in triggering cell-mediated immune reactions.

According to the invention, the fusion antigen is used for the immunization of animals. One objective of the invention is to provide a pharmaceutical composition comprising the fusion antigen of the invention together with a pharmaceutical acceptable carrier. Preferably, the pharmaceutical composition is a T-cell vaccine.

As used herein, the term "T-cell vaccine" refers to a vaccine that can protect a subject from infection by activating cell-mediated immune response. The crucial role of the T-cell vaccine is cytotoxic T-cell (also known as cytotoxic T lymphocyte, $CD8^+$T-cell, and CTL) and memory T-cells ($T_{cm}$ and $T_{em}$).

In one aspect, the invention is related to fusion antigen used as vaccine and method of making them. In one aspect, the method includes: (1) selecting a segment of a virus protein sequence that contains a least one epitope; (2) engineering a DNA fragment encoding the selected segment of the virus protein; (3) inserting the DNA fragment into a *Pseudomonas* Exotoxin A (PE) vector to obtain a chimeric gene plasmid, and expressing the chimeric gene plasmid in a host cell to obtain the chimeric vaccinal virus antigen. The PE vector contains a PE fragment, which has a binding domain and a translocation domain, and a carboxyl terminal moiety, which includes an endoplasmic reticulum (ER) retention sequence. The DNA fragment encoding the selected segment of the virus protein is inserted between the PE fragment and the carboxyl terminal moiety. The chimeric vaccinal virus antigen obtained from the method has a selected virus protein sequence that is not located within any PE domain loops.

The virus antigen is from an infectious virus that is contagious to an animal species. The host cell is at least one selected from the group consisting of a microbe cell, a plant cell and an animal cell. For example, the host cell may be selected from *E. coli* or yeast.

In one embodiment of the invention, the selecting step further comprises the step of retrieving a protein sequence of an infectious virus from a sequence database. The selected segment of the virus protein sequence comprises at least one antibody-neutralization epitope. In another embodiment of the invention, the selected segment of the virus protein sequence may comprise at least one B cell or T cell-stimulating epitope. The selected segment of the virus protein sequence may be a full-length virus protein sequence or a partial fragment thereof.

In one embodiment of the invention, the engineering step further comprises the steps of: (i) deducing a nucleotide sequence from the selected segment of the virus protein sequence; (ii) designing more than one pair of primers from the deduced nucleotide sequence, wherein at least one pair of the primers are complementary to each other at 3' ends thereof; and (iii) performing more than one round of polymerase chain reactions (PCRs), of which the first round PCR is a non-DNA-template PCR, thereby generating the DNA fragment encoding the selected fragment of the virus protein sequence from the primers.

In another embodiment of the invention, the step of deducing a nucleotide sequence further comprises the step of modifying at least one of genetic codons without altering the amino acid encoded, thereby enhancing expression of the chimeric vaccinal virus-antigen in the host cell. The step of deducing a nucleotide sequence may further comprises the step of deleting or altering a sequence that is capable of inducing immune toxicity and/or allergy in an animal.

Yet in another embodiment of the invention, the selecting step selects more than one segment of the virus protein sequence, and the engineering step generates more than one DNA fragment encoding the more than one segment of the virus protein sequence, respectively, and the more than one DNA fragment is ligated to form a DNA fragment for subsequent cloning into the PE vector.

In another embodiment of the invention, the PE fragment contains domains Ia, II and Ib, and the DNA fragment encoding the selected segment of the virus protein sequence is inserted at the 3' end of the domain Ib. The DNA fragment encoding the selected segment of the virus protein is not located within a sequence loop. Further in another embodiment of the invention, the PE fragment is devoid of PE domain III sequence.

The invention is also related to a chimeric vaccinal virus antigen prepared according to the aforementioned method, in which the chimieric virus antigen contains: (a) a PE fragment comprising a binding domain and a translocation domain; (b) a protein or peptide fragment selected from a virus protein sequence; and (c) a carboxyl terminal moiety comprising an endoplasmic reticulum retention sequence. The antigen is not located within a sequence loop.

In another aspect, the invention is related to a method of making a chimeric vaccinal virus antigen, in which the method comprises all the same steps as aforementioned except the step (3), in which the DNA fragment is inserted into a *Pseudomonas* Exotoxin A (PE) vector that does not contain an ER retention sequence at the carboxyl terminal moiety. Thus, the resulted chimeric vaccinal virus antigen does not present an ER retention sequence. See U.S. patent application Ser. No. 11/183,796, which is incorporated herein by reference in its entirety.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

The invention is related to a platform for generating a chimeric vaccinal virus antigen that contains a binding domain, a translocating domain, a target antigenic protein or peptide, and a carboxyl terminal domain having an ER retention sequence. The target antigenic protein or peptide is selected from a known protein sequence. Its codons are converted and modified for optimal bacterial expression.

The following embodiments use several peptides of avian influenza virus H5N1 as examples of the target antigens. They are highly conserved regions of viral proteins used to elicit a vaccine response in vivo without causing a viral infection either in researchers designing vaccines or in patients. The target proteins used in the following examples are: H5N1-NS1, H5N1-NP, H5N1-HA, H5N1-M2, and HSN1-NA.

Preparation of the Expressed Fusion Protein

The target subunit protein M2 had poor expression in *E. coli*, possibly due to the toxicity of the fusion protein itself to the bacteria. To deal with this problem, the hydrophobic regions of M2 were removed, and the hydrophilic regions of the protein were retained. The resulting truncated M2 protein is referred to as H5N1-eM2. The HSN1-eM2 construct could be expressed in large scale in *E. coli*. Sequence comparisons indicated that the regions of high immunogenicity were retained. The H5N1-M2 related antigens are mainly represented by H5N1-eM2 in the examples.

Selection of target peptide sequence segments. The amino acid sequences of H5N1-NS1, H5N1-NP, H5N1-HA, H5N1-M2, and H5N1-NA were retrieved from the National Center of Biotechnology Information (NCBI, USA) database. The peptide sequence was entered into software (i.e., DNA strider V1.0) for evaluation of the hydrophobicity to predict protein folding. The desired antigenic sequence must at least be located on the surface of the protein and be able to contact with water, so hydrophilic regions were selected to proceed with the preparation of the synthesized peptides. Note that this Example is not set to limit the selection of desired regions, and other regions able to induce similar effects are covered by the claims of the present invention.

Several hydrophilic peptide sequence segments from various target proteins were selected. They are: one from H5N1-NS1 (SEQ ID NO: 1), four from H5N1-NP (SEQ ID NOs: 2-5), one from H5N1-HA (SEQ ID NO: 6), H5N1-eM2 (SEQ ID NO: 7), and H5N1-NA (SEQ ID NO: 8) each.

Codon substitutions without altering the original amino acid sequence of the selected peptide segment were made for avoiding spurious restriction sites and for optimal expression in E. coli. Restriction site linkers were added at the ends of the peptide segment-encoding DNA sequence for insertion into the expression vector containing PE(ΔIII) and a carboxyl terminal moiety having an ER retention sequence.

The DNA fragments of the modified nucleic acid sequence encoding target antigen were synthesized by polymerase chain reaction using primers listed in Table 1. Non-DNA template PCR was performed. After the first run PCR, 0.01-1 μl of the DNA product were used as a DNA template for the second run PCR, in which the second primer pair was added together with dNTPs, reagents and Pfu polymerase. The remaining primer pairs were sequentially added in this manner at the subsequent runs of PCR until the target antigen-encoding DNA fragments were respectively synthesized.

All synthesized nucleotide fragments were analyzed by electrophoresis to check if they were of the expected sizes. H5N1-NS (396 bp); H5N1-NP (four fragments: a (256 bp), b (365 bp), c (464 bp), and d (488 bp) were used); H5N1-HA (486 bp); H5N1-eM2; and H5N1-HA (501 bp).

TABLE 1

| Target antigen | Number of forward primers | SEQ ID NO. | Number of reverse primers | SEQ ID NO. |
|---|---|---|---|---|
| NS1 | 6 | 9-14 | 6 | 15-20 |
| NP-a | 4 | 21-24 | 4 | 25-28 |
| NP-b | 6 | 29-34 | 6 | 35-40 |
| NP-c | 8 | 41-48 | 8 | 49-56 |
| NP-d | 8 | 57-64 | 8 | 65-72 |
| HA | 8 | 73-80 | 8 | 81-88 |
| eM2 | 4 | 89-92 | 1 | 93 |
| NA | 8 | 94-101 | 8 | 102-109 |

The eight DNA fragments were ligated into EcoRI and XhoI restriction enzymes digested pET vector so that the fusion protein was added between the PE(ΔIII) fragment and the C-terminal moiety containing an ER retention sequence (FIGS. 1A-1H). Plasmids containing inserts were respectively transformed into E. coli and clones selected for by ampicillin resistance.

The clones were grown up from 2 ml of glycerol storage stocks by inoculation into 500 ml flask containing 200 ml of LB with 500 μg/ml Ampicillin. The flasks were shaken at 150 rpm and 37° C., until the cultures had an $OD_{600}$ of 1.0±0.3.

Aliquots of 50 ml were inoculated in each one of eight sterilized 3000 ml flasks containing 1250 ml LB fortified with 500 μg/ml of Ampicillin and 50 ml 10% glucose, incubated in a 37° C. rotating incubator and shaken at 150 rpm for 2-3 hours. IPTG was then added to a final concentration of 50ppm, and the culture was incubated at 37° C. with shaking for another 2 hours to complete-the protein induction.

The antigen protein fragments were extracted from the inclusion bodies by an 8M urea extraction method. The antigens were quantified by densitometry of Coumassie blue stained SDS-PAGE. 0.03±0.003 mg of antigen protein was used for high-dose injections, and 0.01±0.0001 mg was used for low-dose injections. For each 10 liters of bacterial 5 culture about 300-400 mg of antigen was obtained, which was sufficient for 3000-9000 injections.

Vaccine Preparations

In a class 100 laminar flow, each antigen was dissolved in 8M urea to a final volume 40 ml and mixed with an equal volume of A 206 adjuvant. The mixture was stirred at 50 rpm for 10 minutes, sterilize water was added and the stirring speed was increased to 100 rpm for one hour. The antigen was dispensed into each injection vial, which was then sealed and labeled. One hundred doses of Avian Influenza vaccine were obtained.

Example 1

Antibody Titer Test

To demonstrate that immunization with recombinant vaccines results in serum antibodies, fusion antigen PE-H5N1-eM2-K3 was used as an example. Three doses were used for immunization: high, 0.3±0.03 mg; median, 0.03±0.003 mg; and low, 0.01±0.0001 mg. The different amounts of antigen were mixed with A206 adjuvant and immunized three groups of twelve Balc/C mice. Each mouse received 3 to 4 immunizations at two-week intervals.

Figure 2:
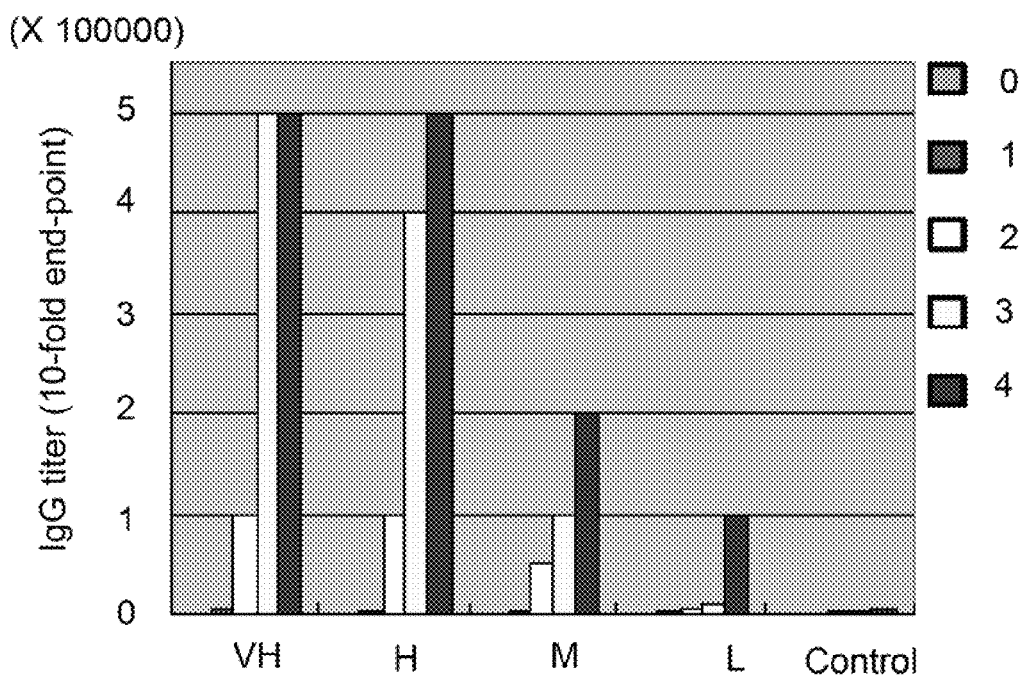
FIG. 2 is a chart showing antibody titers elicited by chimeric antigen PE-eM2-K3 at different doses and immunization times.

Blood samples were taken and the serum assayed in an ELISA for the titer of Anti-M2 specific antibodies using serial ten-fold dilutions. Anti-M2 specific IgG antibody titer was detected after the second round of immunization. M2 anti-specific IgG, an antibody titer was detected after the second round of immunization. The very high dose (VH) (0.1±0.01 mg) and high-dose injections (H) (0.3±0.03 mg) induced similar titers after the third round immunization and reached a plateau after the fourth round. The low dose of injection induced a lower titers, but was still detectable at a 1:10,0000 dilution after the fourth round immunization (FIG. 2).

Example 2

Vaccinal Immunization Tests of Egg-laying Leghorn Chickens

Figure 3:
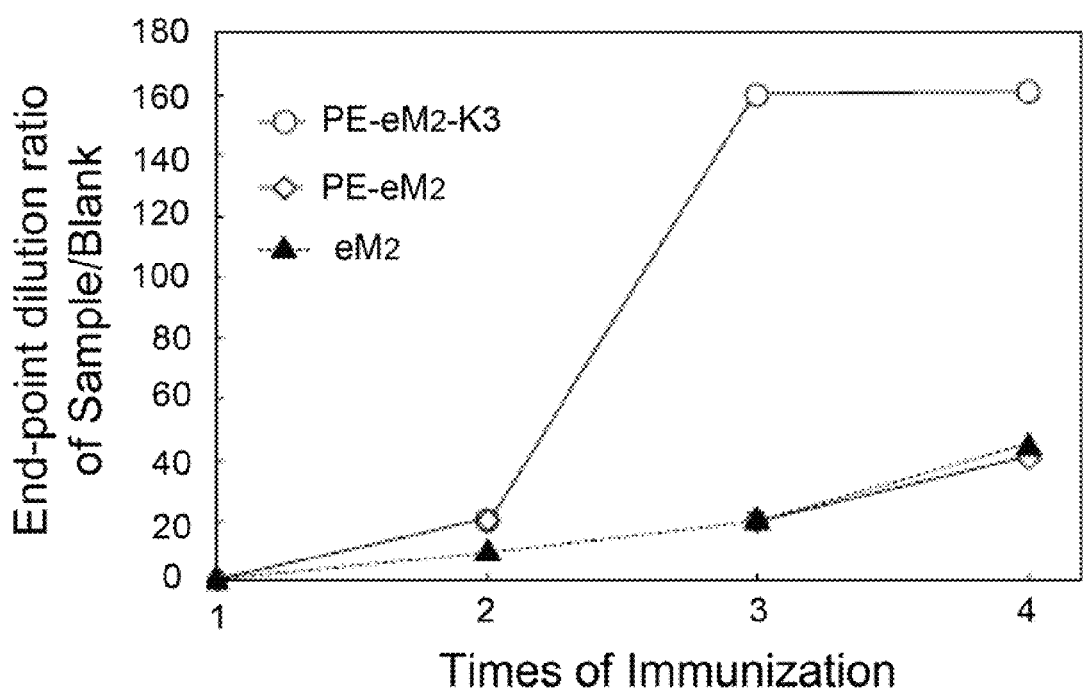
FIG. 3 is a chart showing antibody titers elicited by chimeric antigens PE-eM2-K3, PE-eM2, and antigen eM2, respectively, at different immunization times.

Taking PE-H5N1-eM2-K3 as an example, 0.1±0.01 mg of the fusion antigen was mixed with appropriate adjuvant, and administered to a Leghorn chicken at egg-laying stage. As shown in FIG. 3, after three to four immunizations with PE-H5N1-eM2-K3, high-titers of anti-avian influenza antibodies accumulated in the yolks using a serial dilution ELISA assay. When PE-H5N1-eM2 or eM2 subunit proteins were used in vaccines, the IgY titers were very low, about 10-40 times the non-immunized control group.

Example 3

Immunization of ICR Mice with H5N1 Target Fusion Protein Vaccines and Virus Challenge Tests In this example, the fusion proteins expressed were the conserved common immunogens of the H5N1 type influenza virus. According to the general knowledge of the art, H1N1 shares characteristics in common with any N1-type virus, such as H5N1. Hence, vaccines comprising the fusion proteins which are conserved common immunogens of the H5N1 type influenza virus can protect a host against both of H1N1 type and H5N2 type viruses. Because H5N1 type influenza virus is extremely pathogenic in humans, the containment requirements make it unsuitable for experimentation. Demonstration that a fusion protein vaccine containing common immunogens of the H5N1 type influenza can protect a host against both H1N1 and H5N2 type viruses should however be an adequate approach for a person having the ordinary skills of the art.

Challenge with H1N1 Type Human Influenza Virus

The individual fusion proteins were mixed with adjuvant at a pre-determined dose (High dose, 0.1±0.01 mg; Low dose, 0.01±0.001 mg); and administered to groups of six ICR mice.

After 3 to 4 immunizations, the mice were challenged with H1N1. The health of the mice was monitored and at four days post challenge saliva was assayed for virus excretion. The results are in the table below:

TABLE 2

| Group | Fusion protein | No. of Mice immunized | No. of mice excreting virus | No. of ill mice |
|---|---|---|---|---|
| I | PE-H5N1-eM2-K3 (H) | 6 | 2 | 1 |
| II | PE-H5N1-NP-(a + b + c + d)-K3 (H) | 6 | 2 | 0 |
| III | PE-H5N1-HA-K3 (H) | 6 | 5 | 3 |
| IV | PE-H5N1-NS1-K3 (L) | 6 | 4 | 4 |
| V | None (Control) | 6 | 5 | 5 |

Fewer mice-immunized with the fusion proteins tested positive for virus in their saliva at 4 days post immunization than the control group did. Although high doses of PE-H5N1-eM2-K3 and PE-H5N1-NP-(a+b+c+d)-K3 were more effective, PE-H5N1-NS1-K3 at a low dose was still more effective than the control. These results show that immunization with fusion proteins of the invention can protect mice against influenza virus H1N1 exposure.

Challenge with H5N2 Subtype of Avian Influenza Virus

The individual fusion proteins were mixed with adjuvant at a pre-determined dose (high dose: 0.1±0.01 mg; low dose: 0.01±0.001 mg); and administered to groups of five ICR mice.

After 3 to 4 immunizations, the mice were challenged with H5N2. The health of the mice was monitored and at four days post challenge saliva was assayed for virus excretion. The results are in the table below:

TABLE 3

| Group | Fusion protein | No. of mice immunized | No. of mice excreting virus | No. of ill mice |
|---|---|---|---|---|
| I | PE-H5N1-eM2-K3 (H) | 5 | 2 | 1 |
| II | PE-H5N1-NP-(a + b + c + d)-K3 (H) | 5 | 2 | 0 |
| III | PE-H5N1-HA-K3 (H) | 5 | 2 | 0 |
| IV | PE-H5N1-NS1-K3 (L) | 5 | 2 | 0 |
| V | PE-H5N1-NA0-K3 (H) | 5 | 2 | 0 |
| VI | Blank | 5 | 4 | 2 |

Fewer mice immunized with the fusion proteins tested positive for virus in their saliva at 4 days post immunization than the control group. These results show that immunization with fusion proteins can protect mice against H5N2 influenza viral exposure.

At 14 days post-challenge, the mice immunized with H5N1-eM2-K3 were sacrificed, the lungs processed for making pathological sections, and the severity of interstitial pneumonia was determined. The results are shown in the table below.

TABLE 4

| Group | mice No. | total scores |
|---|---|---|
| unimmunized and challenged with virus H5N2 | BK-1 | 7 |
| | BK-2 | 6 |
| | BK-3 | 7 |
| | BK-4 | 5 |
| immunized with PE-H5N1-eM2-K3 and challenged with virus H5N2 | 8-1 | 2 |
| | 8-2 | 3 |
| | 8-3 | 3 |
| | 8-4 | 4 |
| unimmunized and unchallenged | CTL-1 | 1 |
| | CTL-2 | 1 |
| | CTL-3 | 1 |
| | CTL-4 | 1 |

Point Scoring:
minimal = 1
mild = 2,
moderate = 3
severe = 4
multifocal = 1
diffuse = 2
subacute = 1

Figure 4:
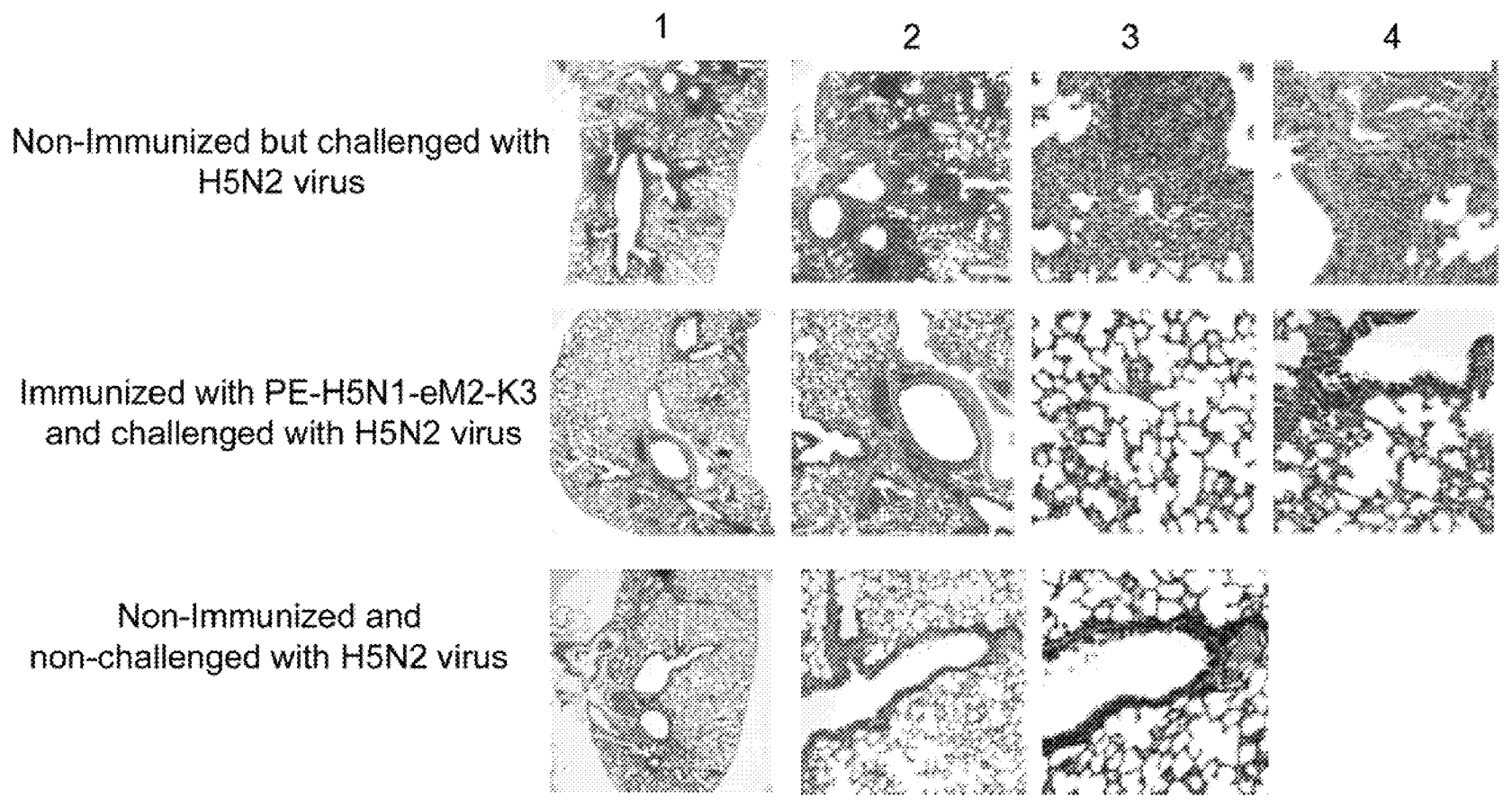

The most severe mouse was scored with 7 points and the mouse with little interstitial pneumonia scored as 3 points. Samples of the histochemistry are shown in FIG. 4. The PE-H5N1-eM2-K3 immunized mice had lower pneumonia scores than the unimmunized ones.

Example 4

Field Trial in a Chicken Farm Infected with H5N2 Type Avian Influenza Virus

Figure 5:
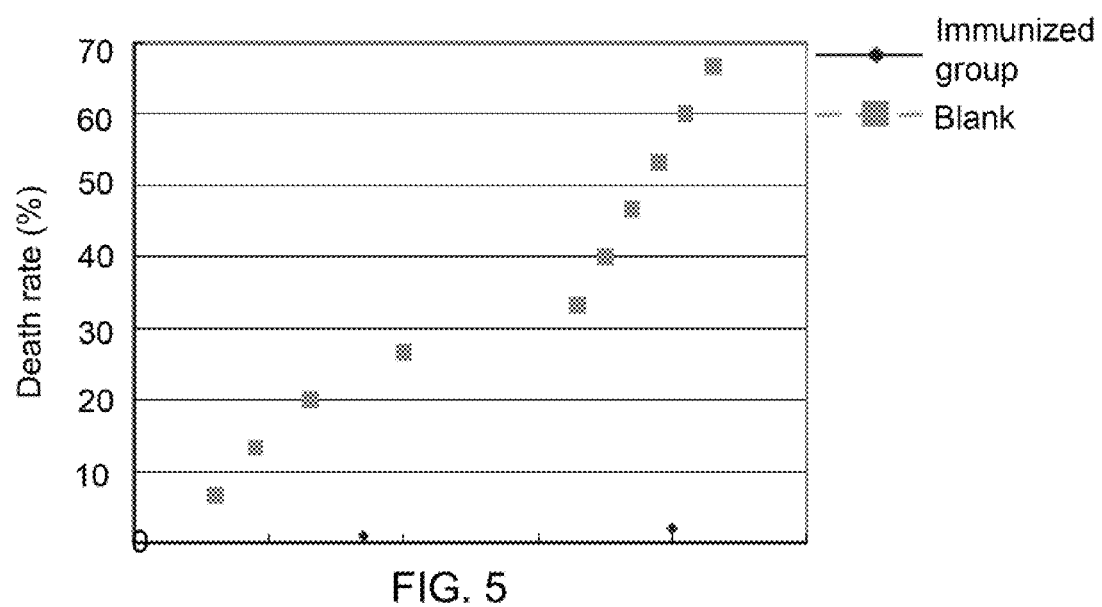
FIG. 5 is a chart showing the death rate dramatically decreased in chickens during the immunization period.

A field trial of the vaccine was performed in a chicken farm having an outbreak of H5N2 type avian influenza virus. The chickens were immunized with a dose of a complex vaccine containing 0.05 mg PE-H5N1-eM2-K3, 0.01 mg PE-H5N1-NP-a-K3, 0.01 mg PE-H5N1-NP-b-K3, 0.01 mg PE-H5N1-NP-c-K3, 0.01 mg PE-H5N1-NP-d-K3, 0.05 mg PE-H5N1-HA-K3, 0.05 mg PE-H5N1-NA-K3, and 10% ISA206. The chickens were immunized every two weeks in a total of four or five times. As shown in FIG. 5, the death rate in the vaccinated chickens was under 5%, while the control group had a death rate of about 60 to 70%.

Figure 6:
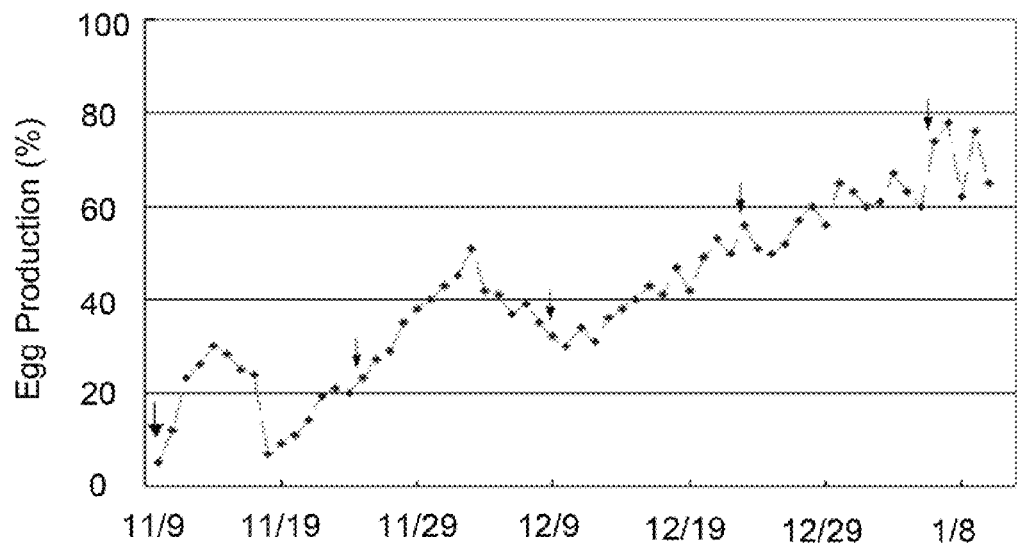
FIG. 6 is a chart showing egg productions in vaccinated chicken during the immunization period.
Figure 7:
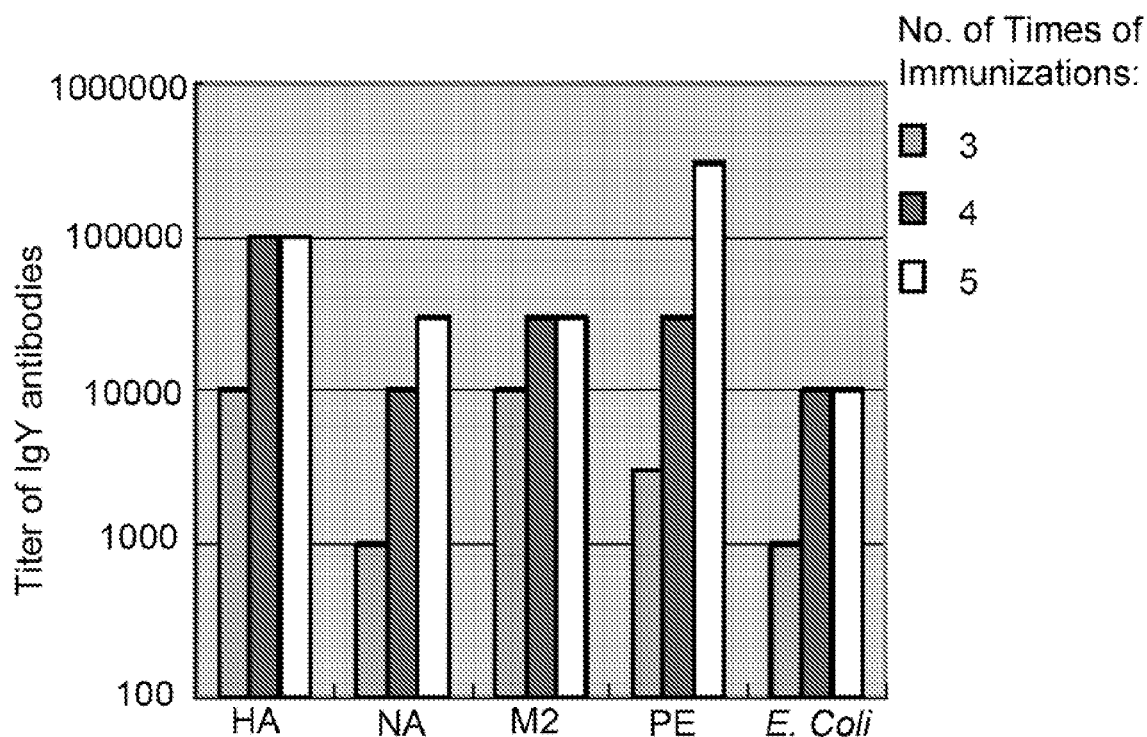
FIG. 7 is a chart showing antibody titers elicited by various antigens at different times of immunizations.
Figure 8:
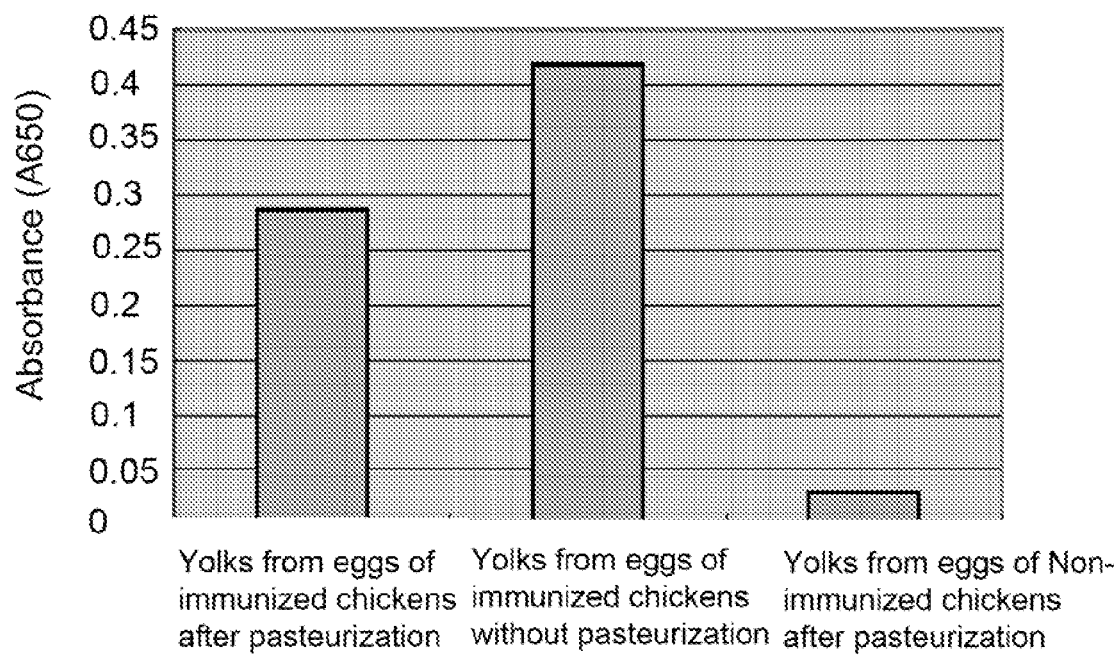
FIG. 8 is a chart showing anti-HA antibody titer.

The production of eggs in the chickens showed an upward trend as the times of immunization increased (FIG. 6). An IgY antibody test was performed on the yolks of the eggs from immunized chickens. The titers of IgY anti HA, NA, M2 PE, and *E. coli* increased as the times of immunization increased (FIG. 7). After five immunizations, the egg yolks had dramatically positive reactions against H5N1-M2 (data was similar to FIG. 8) and H5N1-HA (FIG. 8) even at 500 fold dilutions.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for making a vaccinal virus fusion antigen, comprising:

selecting a segment of a virus protein sequence that comprises at least one epitope;

synthesizing a DNA fragment encoding the selected segment of the virus protein sequence;

inserting the DNA fragment encoding the selected segment of the virus protein sequence into a *Pseudomonas* Exotoxin A (PE) vector to obtain a fusion gene plasmid, in which the PE vector comprises:

(i) a PE fragment comprising a binding domain and a translocation domain and is without a cytotoxic domain; and (ii) a carboxyl terminal moiety comprising an endoplasmic reticulum retention sequence, wherein the DNA fragment encoding the selected segment of the virus protein sequence is inserted between the PE fragment and the carboxyl terminal moiety, thereby generating a fusion gene plasmid; and expressing the fusion gene plasmid in a host cell to obtain the vaccinal virus fusion antigen, wherein the vaccinal virus fusion antigen comprises:

(i) the PE fragment;

(ii) the selected segment of the virus protein sequence; and (iii) the carboxyl terminal moiety comprising the endoplasmic reticulum retention sequence.

2. The method of claim 1, wherein the carboxyl terminal moiety comprises the amino acid sequence of SEQ ID NO: 110.

3. The method of claim 2, wherein the virus antigen is selected from an infectious virus that is contagious to an animal species.

4. The method of claim 2, wherein the virus protein sequence comprises porcine reproductive and respiratory syndrome virus (PRRSV) ORF7.

5. The method of claim 2, wherein the host cell is at least one selected from *E. coli*.

6. The method of claim 2, wherein the PE fragment comprises domains Ia, II and Ib, and the DNA fragment encoding the selected segment of the virus protein sequence is inserted at the 3' end of the domain Ib.

7. A method for making a vaccinal virus fusion antigen, comprising:

selecting a segment of a virus protein sequence that comprises at least one epitope;

synthesizing a DNA fragment encoding the selected segment of the virus protein sequence;

inserting the DNA fragment encoding the selected segment of the virus protein sequence into a *Pseudomonas* Exotoxin A (PE) vector to obtain a fusion gene plasmid, in which the PE vector comprises:

(i) a PE fragment comprising a binding domain and a translocation domain and is without a cytotoxic domain; and (ii) a carboxyl terminal moiety comprising the amino acid sequence of SEQ ID NO: 112, wherein the DNA fragment encoding the selected segment of the virus protein sequence is inserted between the PE fragment and the carboxyl terminal moiety, thereby generating a fusion gene plasmid; and expressing the fusion gene plasmid in a host cell to obtain the vaccinal virus fusion antigen, wherein the vaccinal virus fusion antigen comprises:

(i) the PE fragment;

(ii) the selected segment of the virus protein sequence; and (iii) the carboxyl terminal moiety comprising the amino acid sequence of SEQ ID NO: 112.

8. The method of claim 7, wherein the virus protein sequence comprises a porcine reproductive and respiratory syndrome virus (PRRSV) protein selected from the group consisting of ORF7 and ORF1b.

9. The method of claim 7, wherein the virus protein sequence comprises PRRSV ORF7 protein.

10. The method of claim 7, wherein the virus protein sequence comprises PRRSV ORF1b protein.

11. A method for making a vaccinal virus fusion antigen, comprising:

selecting a segment of a virus protein sequence that comprises at least one epitope;

synthesizing a DNA fragment encoding the selected segment of the virus protein sequence;

inserting the DNA fragment encoding the selected segment of the virus protein sequence into a *Pseudomonas* Exotoxin A (PE) vector to obtain a fusion gene plasmid, in which the PE vector comprises:

(i) a PE fragment comprising a binding domain and a translocation domain and is without a cytotoxic domain; and (ii) a carboxyl terminal moiety comprising the amino acid sequence of SEQ ID NO: 110 or 111, wherein the DNA fragment encoding the selected segment of the virus protein sequence is inserted between the PE fragment and the carboxyl terminal moiety, thereby generating a fusion gene plasmid; and
expressing the fusion gene plasmid in a host cell to obtain the vaccinal virus fusion antigen;
wherein the vaccinal virus fusion antigen comprises:
(i) the PE fragment;
(ii) the selected segment of the virus protein sequence; and
(iii) the carboxyl terminal moiety comprising the amino acid sequence of SEQ ID NO: 110 or 111.

* * * * *